United States Patent [19]

Margel

[11] Patent Number: 4,677,138
[45] Date of Patent: Jun. 30, 1987

[54] HIGH YIELD PROCESS FOR PRODUCING POLYALDEHYDE MICROSPHERES

[75] Inventor: Shlomo Margel, Rehovot, Israel

[73] Assignee: Yeda Research and Development Co., Ltd., Rehovot, Israel

[21] Appl. No.: 662,722

[22] Filed: Oct. 19, 1984

[30] Foreign Application Priority Data

Oct. 19, 1983 [IL] Israel ........................................ 70004

[51] Int. Cl.[4] ............................................... C08G 2/02
[52] U.S. Cl. ................................... 522/178; 523/223; 526/315
[58] Field of Search ........................ 526/315; 523/223; 204/159.21; 522/178

[56] References Cited

U.S. PATENT DOCUMENTS 3,105,801 10/1963 Bell et al. ....................... 204/159.21
4,413,070 11/1983 Rembaum .......................... 526/315
4,438,239 3/1984 Rembaum et al. ............. 204/159.21
4,534,996 8/1985 Rembaum et al. ............. 204/159.21

OTHER PUBLICATIONS

Journal of Cellular Science, vol. 56, pp. 157–175 (1982), Margel et al.

*Primary Examiner*—Melvyn I. Marquis
*Attorney, Agent, or Firm*—John P. White

[57] ABSTRACT

Homopolymeric polyaldehyde microspheres can be prepared in yields of up to about 90% by preparing an aqueous solution consisting essentially of a suitable concentration of an $\alpha,\beta$-ethylenically unsaturated aldehyde and a suitable concentration of an appropriate surfactant under suitable conditions such that the surfactant has a net electrostatic charge. The solution, which may also contain a ferrofluidic material, fluorescent dye or additional solvent, is then irradiated under an inert atmosphere with a sufficient dose of $\gamma$-radiation to effect polymerization and the monodisperse homopolymeric polyaldehyde microspheres so produced are recovered. Copolymeric polyaldehyde microspheres can be prepared by adding to the solution a suitable concentration of a copolymerizable comonomer before initiating polymerization.

Monodisperse homopolymeric or copolymeric polyaldehyde microspheres useful for affinity chromatography, cell labeling, cell separation and diagnostic purposes can thus be prepared in significantly higher yield than was previously obtainable.

15 Claims, No Drawings

HIGH YIELD PROCESS FOR PRODUCING POLYALDEHYDE MICROSPHERES

BACKGROUND OF THE INVENTION

Polymeric microspheres are a well-known tool for studying biological and biochemical systems. They are useful in such applications as affinity chromatography cell labeling, cell separation and diagnostic methods. Polyacrolein microspheres have been found to be particularly useful in such applications because of their stability and ease of derivatization [Margel, S., Beitler, U. and Ofarim, M., J. Cell Science 56:157-175 (1982)].

It is known that microspheres can be prepared from $\alpha,\beta$-ethylenically unsaturated aldehydes by several methods and that the chemical structure of the resultant microspheres depends on the method of preparation. Polyacrolein microspheres may be prepared, for example, by base-catalyzed polymerization of acrolein in the presence of the ionic surfactant PGL-NaHSO$_3$ [Margel, S. et al., J. Cell Sci. 56:157-175 (1982)]. It is also known that polyacrolein microspheres may be prepared by radiation-initiated polymerization of acrolein in the presence of non-ionic surfactants [Rembaum, A., Yen, R. C. K., Kempner, D. H. and Ugelstad, J., J. Immunol. Methods 52:341-351 (1982); U.S. Pat. No. 4,413,070 (1983); and Margel, S. et al., J. Cell Sci. 56:157-175 (1982)].

The polyacrolein microspheres prepared by base-catalyzed polymerization and those prepared by radiation-initiated polymerization differ from one another in chemical structure presumably because the two methods involve different reaction mechanisms. Larger stable microspheres may be prepared by the base-catalyzed method than by the radiation-initiated method, but the radiation-initiated microspheres contain more free aldehyde groups. Additionally, the two types of polyacrolein microspheres differ from one another both qualitatively and quantitatively with respect to internal crosslinking and hydrophilicity.

Because of the greater concentration of free aldehyde groups on radiation-initiated polyacrolein microspheres, such microspheres may be preferred for certain applications in which a high degree of ligand-binding activity is desired. Widespread use of radiation-initiated polyacrolein microspheres, especially homopolymeric polyacrolein microspheres, however, has been hindered by heretofore unresolved preparative problems, foremost of which is the low yield in which the microspheres are obtained (e.g., 17.6% yield, Rembaum, U.S. Pat. No. 4,413,070, issued Nov. 1, 1983). Moreover, attempts to increase the yield of microspheres by using a higher concentration of monomer or by using a higher dose of radiation result only in intractable agglomeration of the starting materials.

A method has now been unexpectedly discovered for producing homopolymeric polyaldehyde microspheres in significantly improved yield.

SUMMARY OF THE INVENTION

The present invention provides a method for preparing monodisperse homopolymeric polyaldehyde microspheres in high yield, preferably in yields between about 60 percent and 90 percent. According to this method, a solution is prepared consisting essentially of a suitable concentration, e.g. up to about 10% v/v of an $\alpha,\beta$-ethylenically unsaturated aldehyde such as acrolein, methacrolein or crotonaldehyde, and a suitable concentration of an appropriate surfactant under conditions such that the surfactant has a net electrostatic charge. Preferably the surfactant is present in a concentration from about 0.02-5.0% (w/v) based on the volume of the solution. Appropriate surfactants include surfactants which are substantially non-ionic at a neutral pH, e.g. polyethers such as polyethylene oxide (PEO) or polyethylene glycol (PEG), and surfactants which are ionic at a neutral pH, e.g. polycarboxylic acids such as polyacrylic acid or polymethylacrylic acid. If desired, one or more of a ferrofluidic material, e.g., Fe$_3$O$_4$; fluorescent dye; or cosolvent may be added to the solution. The solution is then irradiated under an inert atmosphere such as that provided by nitrogen or argon with a dose of $\gamma$-radiation sufficient to effect polymerization. The monodisperse homopolymeric polyaldehyde microspheres are then recovered. By this method, various types of homopolymeric polyaldehyde microspheres may be prepared in high yields.

This invention also provides a method for producing monodisperse copolymeric polyaldehyde microspheres in high yield. According to this method an aqueous solution is prepared containing an $\alpha,\beta$-ethylenically unsaturated aldehyde, a suitable concentration of a copolymerizable comonomer and a suitable amount of a polycarboxylic acid, e.g. polyacrylic or polymethacrylic acid, at a pH above a value of about 3.0. The solution is then irradiated with a dose of $\gamma$-radiation sufficient to effect polymerization and the monodisperse copolymeric polyaldehyde microspheres so produced are recovered. Suitably the comonomer is an $\alpha,\beta$-ethylenically unsaturated alkenyl, arylalkenyl or heteroalkyl ether, alcohol, thiol, carboxylic acid, ester, amide, amine, carbamate, aldehyde or ketone.

Thus, by the methods of this invention monodisperse homopolymeric or copolymeric polyaldehyde microspheres useful in such applications as affinity chromatography, cell labeling, cell separation and diagnostic methods may be obtained.

DETAILED DESCRIPTION OF THE INVENTION

Monodisperse homopolymeric polyaldehyde microspheres may be produced by first preparing an aqueous solution consisting essentially of a suitable concentration of an $\alpha,\beta$-ethylenically unsaturated aldehyde, and a suitable concentration of an appropriate surfactant under suitable conditions such that the surfactant has a net electrostatic charge. The solution is then irradiated under an inert atmosphere with a dose of $\gamma$-radiation sufficient to effect polymerization of the aldehyde monomer, and the monodisperse homopolymeric polyaldehyde microspheres so produced are recovered.

Monomers useful as starting materials in the practice of this invention include $\alpha,\beta$-ethylenically unsaturated aldehydes such as acrolein, methacrolein and crotonaldehyde. Acrolein in particular is a preferred starting material. In the practice of this invention, monomer concentrations up to about five percent by volume based upon the volume of the solution are suitable. Higher yields may be obtained, however, by increasing the monomer concentration to about ten percent (v/v), and concentrations between about seven and about ten percent (v/v) are preferred. In contrast to the results obtained with prior methods, agglomeration does not occur to any significant degree at these concentrations because of the greater microsphere stabilization obtained by the method of this invention.

According to this invention the surfactant is added to the solution prior to irradiation in an amount sufficient to achieve a suitable surfactant concentration for stabilizing the microspheres during polymerization, i.e., a concentration greater than the critical micelle concentration. Preferably, the surfactant concentration is between about 0.02 and 5.0 percent by weight based upon the volume of the solution.

Appropriate surfactants useful in this method are those which are capable of bearing a net electrostatic charge, preferably, surfactants containing a heteroatom. Such surfactants include ionic surfactants such as polycarboxylic acids as well as surfactants which are generally considered to be non-ionic, e.g., polyethers.

In one embodiment of this invention the surfactant is a polyether such as polyethylene oxide (PEO) or polyethylene glycol (PEG), and the suitable conditions comprise a pH value between about 1 and about 3.5. In this embodiment the pH of the solution is reduced by the addition of a suitable amount of an acid, e.g., hydrochloric acid. Under appropriately acidic conditions heteroatoms (e.g., oxygen, nitrogen or sulfur) are protonated partially or completely, and the otherwise non-ionic surfactant acquires at least a partial electrostatic charge. As illustrated by the examples provided hereinafter, the presence of a partially or a completely protonated surfactant, e.g., PEO at a pH below about 3.5, minimizes agglomeration and permits the preparation of microspheres in yield of up to 90%. It is believed that these results are due to the enhanced stabilization of the incipient microspheres by both electrostatic and steric interaction between the microspheres and the surfactant.

In another embodiment of the invention, an ionic surfactant such as a polycarboxylic acid, e.g., polyacrylic acid (PA) or polymethacrylic acid (PMA) is used and milder pH conditions may be employed. Thus a pH above a value of about 3.0 is suitable. Unlike non-ionic surfactants such as PEO and PEG, a polycarboxylic acid has inherent electrostatic properties. This electrostatic character is due to the fact that in aqueous solution the acid exists in an equilibrium between a protonated electrostatically neutral carboxylic form and an unprotonated electrostatically charged carboxylic form:

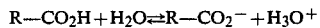

$$R-CO_2H + H_2O \rightleftharpoons R-CO_2^- + H_3O^+$$

The extent of dissociation is evidenced by the fact that an aqueous solution of 0.5% (w/v) PA has a pH value of about 3.3. Similarly, the pH of a 0.5% (w/v) aqueous solution of polymethacrylic acid is about 4.0. Since the degree of dissociation of an acid is pH dependent, the electrostatic stabilizing properties of the polycarboxylic acid can be altered by changing the pH of the aqueous solution. As the pH is lowered the carboxylic ion concentration and thus the electrostatic character of the polycarboxylic acid decrease. On the other hand, as the pH of the solution is increased, the carboxylate ion concentration and the electrostatic stabilizing properties of the surfactant increase. Accordingly, in one embodiment of this invention polyacrylic acid is used as the surfactant and the pH of the solution is adjusted to a value greater than about 3.0 by the addition of an alkaline substance e.g., sodium hydroxide. In another embodiment of this invention polymethacrylic acid is used as the surfactant and the pH is adjusted to a value greater than about 4.0. In presently preferred embodiments using PA or PMA the pH is adjusted to a value between about 5 and 11.

Polymerization is then effected by irradiating the solution with high energy radiation, suitably $\gamma$-radiation, at a temperature between about 0° C. and 100° C., preferably at ambient temperature, under oxygen-excluding conditions, e.g., under an inert atmosphere provided by nitrogen or argon. The radiation may be provided by any convenient source, although cobalt$^{60}$ is presently preferred. While doses of Co$^{60}$ $\gamma$-radiation as low as 0.05 megarads applied at rates as low as 0.12 megarad/hr are capable of initiating polymerization, one of the advantages of this invention is that because of the greater degree of microsphere stabilization obtained under the conditions provided herein much higher doses of radiation and dose rates may be used without agglomeration of the starting materials. Thus, in accordance with this invention doses greater than about 0.7 megarads applied at a rate of up to about 0.24 megarad/hr (4 kilorads/min) are suitable for initiating polymerization. For higher yields, e.g., up to about 90 percent, doses of up to about 2.5 megarads are preferred.

The monodisperse homopolymeric polyaldehyde microspheres so produced are then recovered by conventional means, e.g. by centrifugation.

Where microspheres with additional functionality are desired additional materials may be added to the reaction mixture before initiation of polymerization. Magnetic microspheres, for example, may be prepared in accordance with this invention by adding a ferrofluidic material, e.g., Fe$_3$O$_4$, to the solution. Similarly, fluorescent microspheres may be obtained by adding a fluorescent dye to the solution. The solution may also contain an additional solvent, e.g. dimethylformamide.

This invention also provides a method for producing monodisperse copolymeric polyaldehyde microspheres. In this method an aqueous solution is prepared containing a suitable concentration of an $\alpha,\beta$-ethylenically unsaturated aldehyde, a suitable concentration of a copolymerizable comonomer and a suitable concentration of a polycarboxylic acid surfactant at a pH above a value of about 3.0. The solution is then irradiated under an inert atmosphere with a dose of high energy radiation, suitably $\gamma$-radiation, sufficient to effect polymerization, as in the previously disclosed embodiments and the monodisperse copolymeric polyadehyde microspheres so produced are recovered, e.g. by centrifugation.

Suitable monomers include those previously mentioned, e.g. acrolein, methacrolein and crotonaldehyde, suitably in a concentration of up to about ten percent by volume based on the volume of the solution. Suitable polycarboxylic acid surfactants include polyacrylic acid and polymethacrylic acid, appropriately in concentrations from about 0.02 to about 5 percent by weight based upon the volume of the solution. The copolymerizable comonomer suitable for use in this embodiment may be an $\alpha,\beta$-ethylenically unsaturated alkenyl, arylalkenyl or heteroalkenyl ether, alcohol, thiol, carboxylic acid, ester, amide, amine, carbamate, aldehyde or ketone, suitably in a concentration up to about 50% of the concentration of the $\alpha,\beta$-ethylenically unsaturated aldehyde. By adding such a comonomer to the solution before initiation of polymerization, variations in porosity, hydrophilicity, strength, size and chemical reactivity of the resulting microspheres may be obtained. Ferrofluidic material or a fluorescent dye, or both may also be incorporated in the microspheres as previously described.

Thus, by the methods of this invention monodisperse homopolymeric or copolymeric polyaldehyde microspheres can be produced which are useful in applications such as affinity chromatography, cell labeling, cell separation and diagnostic methods.

The examples which follow are set forth to aid in an understanding of the invention but are not intended to, and should not be construed to, limit in any way the invention as set forth in the claims which follow thereafter.

EXAMPLES

Reagents used in the following examples may be obtained from Aldrich Chemicals Co., Milwaukee, Wis., unless otherwise indicated.

EXAMPLE 1

100 ml of an aqueous solution containing 10% (v/v) acrolein and 0.5% (w/v) polyethylene oxide was deaerated with argon and then irradiated with 0.7 megarad of $\gamma$-radiation. ($Co^{60}$ source, Atomic energy of Canada, Dose rate of 4 kilorad/min.). The yield of the monodisperse microspheres obtained was 25 to 30% (based on the weight of acrolein used). Increasing the dose of radiation to 1 megarad resulted in partial agglomeration of the microspheres, although the yield of the monodisperse microspheres did not change significantly. Increasing the dose to 2 megarads, however, resulted in total agglomeration of the microspheres.

EXAMPLE 2

Example 1 was repeated under more dilute conditions, substituting 5% (v/v) acrolein for the 10% (v/v) acrolein. The yield of the microspheres after an irradiation dose of 1 megarad was approximately 15%. Increasing the irradiation dose to 2 megarads resulted in a total agglomeration.

EXAMPLE 3

Example 1 was repeated substituting surfactants, such as tween 20, polyvinyl alcohol, polyacrylamide and polyvinyl-pyrrolidone for the surfactant polyethylene oxide. The yield of the microspheres obtained after an irradiation dose of 0.25% megarad was approximately 10%. Increasing the irradiation dose to 1 megarad resulted in total agglomeration.

EXAMPLE 4

Example 1 was repeated under various pH conditions. The desired pH was obtained by an appropriate addition of an aqueous solution of HCl or NaOH. Table 1 summarizes the results obtained. For example, at pH 7.5 and pH 5.3 with an irradiation dose of 1.1 megarad, total agglomeration of the microspheres resulted. However, at pH 3.1 and at pH 1.2 and with an irradiation dose of 2 megarads, agglomeration did not occur and the yield was approximately 75%. With further irradiation (2.5 Mrad) the yield increased to approximately 90%.

EXAMPLE 5

Example 4 was repeated substituting 0.2% (w/v) polyethylene oxide for the 0.5% (w/v) polyethylene oxide. After an irradiation dose of 0.5 megarad the microspheres at pH's 7.5, 5.2 and 3.1 were agglomerated, while at pH 1.2 monodisperse microspheres were obtained.

EXAMPLE 6

Example 4 was repeated substituting 0.5% (w/v) polyethylene glycol for the 0.5% (w/v) polyethylene oxide and 7.5% (v/v) acrolein for the 10% (v/v) acrolein. The results obtained (Table 2) were similar to those of Example 4.

TABLE 1

| | Irradiation of Acrolein, 10% (v/v), and PEO, 0.5% (w/v) at Various pH conditions and Radiation Doses | | |
|---|---|---|---|
| pH | Yield[a] after 1.1 megarad of radiation | Yield[a] after 2 megarads of radiation | Yield[a] after 2.5 megarads of radiation |
| 7.5 | — | — | — |
| 5.3 | — | — | — |
| 3.1 | 40% | 75% | 90% |
| 1.2 | 40% | 75% | 90% |

[a]The yield of monodisperse microspheres is based on the amount of acrolein used (by weight); agglomeration is indicated by (—).

TABLE 2

| | Irradiation of Acrolein, 7.5% (v/v), and PEG, 0.5% (w/v) at Various pH conditions and Radiation Doses | |
|---|---|---|
| pH | Yield[a] after 1 megarad of radiation | Yield[a] after 2 megarads of radiation |
| 7.4 | — | — |
| 5.4 | — | — |
| 3.1 | 30% | 65% |
| 1.2 | 30% | 65% |

[a]The yield of monodisperse microspheres is based on the amount of acrolein used (by weight); agglomeration is indicated by (—).

EXAMPLE 7

Example 4 was repeated substituting 0.5% (w/v) polyacrylic acid for the 0.3% (w/v) polyethylene oxide. Table 3 shows that at pH values above 1.2 monodisperse microspheres were obtained in high yield (80%) even at an irradiation dose of 2.2 megarads.

EXAMPLE 8

Example 7 was repeated substituting 0.2% (w/v) polyacrylic acid for the 0.3% (w/v) polyacrylic acid. Similar results were obtained as in Example 7.

EXAMPLE 9

Example 4 was repeated substituting 0.5% (w/v) polymethacrylic acid for the 0.5% (w/v) polyethylene oxide. Table 4 shows that at pH 7.4 and at pH 5.0 monodisperse microspheres were formed in high yield (75%) even at an irradiation dose of 2 megarads.

TABLE 3

| | Irradiation of Acrolein, 10% (v/v), and PA, 0.5% (w/v) at Various pH conditions and Radiation Doses | |
|---|---|---|
| pH | Yield[a] after 1 megarad of radiation | Yield[a] after 2.2 megarads of radiation |
| 7.5 | 35% | 80% |
| 3.3[b] | 35% | 80% |
| 1.2 | — | — |

[a]The yield of monodisperse microspheres is based on the amount of acrolein used (by weight); agglomeration is indicated by (—).
[b]pH obtained for 0.5% PA (w/v) in water.

TABLE 4

Irradiation of Acrolein, 10% (v/v), and PMA, 0.5% (w/v) at Various pH conditions and Radiation Doses

| pH | Yield[a] after 1 megarad of radiation | Yield[a] after 2 megarads of radiation |
|---|---|---|
| 7.4 | 35% | 75% |
| 5.0 | 35% | 75% |
| 4.0[b] | 35% | — |
| 1.2 | — | — |

[a]The yield of monodisperse microspheres is based on the amount of acrolein used (by weight); agglomeration is indicated by (—).
[b]pH obtained for 0.5% PMA (w/v) in water.

What is claimed is:

1. A method for producing monodisperse homopolymeric polyaldehyde microspheres which comprises:
   (a) irradiating an aqueous solution, consisting essentially of a suitable concentration of an $\alpha,\beta$-ethylenically unsaturated aldehyde and a suitable concentration of an appropriate surfactant prepared under suitable conditions such that the surfactant has a net electrostatic charge, under an inert atmosphere with a dose of $\gamma$-radiation sufficient to effect polymerization; and
   (b) recovering the monodisperse homopolymeric polyaldehyde microspheres so produced.

2. A method according to claim 1, wherein the $\alpha,\beta$-ethylenically unsaturated aldehyde is acrolein, methacrolein or crotonaldehyde.

3. A method according to claim 1, wherein the suitable concentration of the $\alpha,\beta$-ethylenically unsaturated aldehyde is up to about ten percent by volume based on the volume of the solution.

4. A method according to claim 1, wherein the suitable concentration of the surfactant is from about 0.02 percent to about 5 percent by weight based upon the volume of the solution.

5. A method of claim 1, wherein the surfactant is a polyether and the suitable conditions comprise a pH value between about 1 and about 3.5.

6. A method according to claim 5, wherein the surfactant is polyethylene oxide or polyethylene glycol.

7. A method according to claim 1, wherein the surfactant is a polycarboxylic acid and the pH of the solution is above a value of about 3.0.

8. A method according to claim 7, wherein the polycarboxylic acid is polyacrylic acid or polymethacrylic acid.

9. A method according to claim 1, wherein the source of the radiation is $Co^{60}$ and the sufficient dose is between about 0.7 and about 2.5 megarads.

10. A method according to claim 1, wherein the solution additionally contains a ferrofluidic material.

11. A method according to claim 1, wherein the ferrofluidic material is $Fe_3O_4$.

12. A method according to claim 1, wherein the solution additionally contains a fluorescent dye.

13. A method according to claim 1, wherein the solution contains an additional solvent.

14. A method for producing monodisperse copolymeric polyaldehyde microspheres which comprises:
    (a) irradiating an aqueous solution, containing a suitable concentration of an $\alpha,\beta$-ethylenically unsaturated aldehyde, a suitable concentration of a copolymerizable comonomer and a suitable concentration of a carboxylic acid surfactant prepared at a pH above a value of about 3.0, under an inert atmosphere with a dose of $\gamma$-radiation sufficient to effect polymerization; and
    (b) recovering the monodisperse copolymeric polyadehyde microspheres so produced.

15. A method according to claim 14, wherein the comonomer is an $\alpha,\beta$-ethylenically unsaturated alkenyl, arylalkenyl or heteroaryl ether, alcohol, thiol, carboxylic acid, ester, amide, amine, carbamate, aldehyde or ketone.

* * * * *